(12) United States Patent  (10) Patent No.: US 7,416,301 B2
Hanebuchi et al.  (45) Date of Patent: Aug. 26, 2008

(54) EYE REFRACTIVE POWER MEASUREMENT APPARATUS

(75) Inventors: Masaaki Hanebuchi, Nukata-gun (JP); Mitsuhiro Gono, Nukata-gun (JP)

(73) Assignee: Nidek Co., Ltd., Aichi-ken (JP)

( * ) Notice: Subject to any disclaimer, the term of this patent is extended or adjusted under 35 U.S.C. 154(b) by 282 days.

(21) Appl. No.: 11/013,694

(22) Filed: Dec. 17, 2004

(65) Prior Publication Data

US 2005/0157261 A1 Jul. 21, 2005

(30) Foreign Application Priority Data

Dec. 25, 2003 (JP) ............................. 2003-430787

(51) Int. Cl.
*A61B 3/10* (2006.01)
(52) U.S. Cl. ................... 351/205; 351/200; 351/211
(58) Field of Classification Search ................ 351/200, 351/211, 205, 221, 246
See application file for complete search history.

(56) References Cited

U.S. PATENT DOCUMENTS 5,483,305 A * 1/1996 Kohayakawa ............... 351/243
5,500,697 A * 3/1996 Fujieda ....................... 351/212
5,886,780 A * 3/1999 Fukuma et al. .............. 356/128
6,471,691 B1 * 10/2002 Kobayashi et al. ........... 606/4
6,695,450 B2 * 2/2004 Hirohara et al. ............. 351/211
2001/0028438 A1 * 10/2001 Matsumoto ................. 351/206

FOREIGN PATENT DOCUMENTS

| JP | 5-31075 A | 2/1993 |
| JP | 8-103413 A | 4/1996 |
| JP | 11-225963 | 8/1999 |
| JP | 2002-17676 A | 1/2002 |

* cited by examiner

*Primary Examiner*—Ricky L Mack
*Assistant Examiner*—James R Greece
(74) *Attorney, Agent, or Firm*—Oliff & Berridge, PLC

(57) ABSTRACT

An eye refractive power measurement apparatus capable of measuring even an eye with a small pupil diameter with accuracy and stability. The apparatus has a measurement optical system including a projection optical system, having a light source, for projecting spot-shaped measurement light onto a fundus and a photo-receiving optical system, having a photodetector, for photo-receiving the measurement light reflected from the fundus via a peripheral pupillary portion, a calculation part which obtains the eye reflective power based on an output from the photodetector, a light deflection member, an arrangement of which in the measurement optical system being prevented from having a positional relationship optically approximately conjugate with a pupil, and a rotation unit which rotates the light deflection member about a measurement optical axis of the measurement optical system.

10 Claims, 6 Drawing Sheets

EYE REFRACTIVE POWER MEASUREMENT APPARATUS

BACKGROUND OF THE INVENTION

1. Field of the Invention

The present invention relates to an eye refractive power measurement apparatus for measuring eye refractive power of an eye of an examinee objectively.

2. Description of Related Art

Conventionally, there is known an eye refractive power measurement apparatus which projects spot-shaped measurement light onto a fundus via a central pupillary portion and photo-receives the measurement light reflected from the fundus via a peripheral pupillary portion using a two-dimensional photodetector or the like to obtain eye refractive power based on a photo-receiving result thereof. In such an apparatus, in order to ensure measurement accuracy, the measurement light reflected from the fundus is arranged to be photo-received via a ring-shaped region of 2 mm in inside diameter and 3 mm in outside diameter on a pupillary surface.

However, if a pupil diameter is smaller than the ring-shaped region, sometimes measurement cannot be performed. Therefore, to cope with this problem, there is proposed an apparatus which rotates a measurement part including a measurement optical system so as to revolve about a pupil center (see Japanese Patent Application Unexamined Publication No. 2002-17676).

However, the apparatus which rotates the entire measurement part including the measurement optical system involves extensive driving and is inappropriate for high-speed rotation. In addition, as a fixation target presenting optical system for presenting a fixation target to an eye is included in the measurement part, if the measurement part is rotated, the presented fixation target is also unintentionally rotated; therefore, measurement cannot be performed in a stable fixation state. Thus, this kind of apparatus is not in the actual use.

Further, to deal with an eye with a small pupil diameter, it is conceivable that the ring-shaped region on the pupillary surface is made even smaller. In this case, however, corneal reflection or crystalline lens reflection of the projected measurement light tends to become noise, and for an ordinary eye with a large enough pupil diameter (a normal eye), measurement accuracy is sometimes contrarily lowered.

SUMMARY OF THE INVENTION

An object of the invention is to overcome the problems described above and to provide an eye refractive power measurement apparatus capable of measuring even an eye with a small pupil diameter with accuracy and stability.

To achieve the objects and in accordance with the purpose of the present invention, an eye refractive power measurement apparatus has a measurement optical system including a projection optical system, having a light source, for projecting spot-shaped measurement light onto a fundus and a photo-receiving optical system, having a photodetector, for photo-receiving the measurement light reflected from the fundus via a peripheral pupillary portion, a calculation part which obtains the eye reflective power based on an output from the photodetector, a light deflection member, an arrangement of which in the measurement optical system being prevented from having a positional relationship optically approximately conjugate with a pupil, and a rotation unit which rotates the light deflection member about a measurement optical axis of the measurement optical system.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
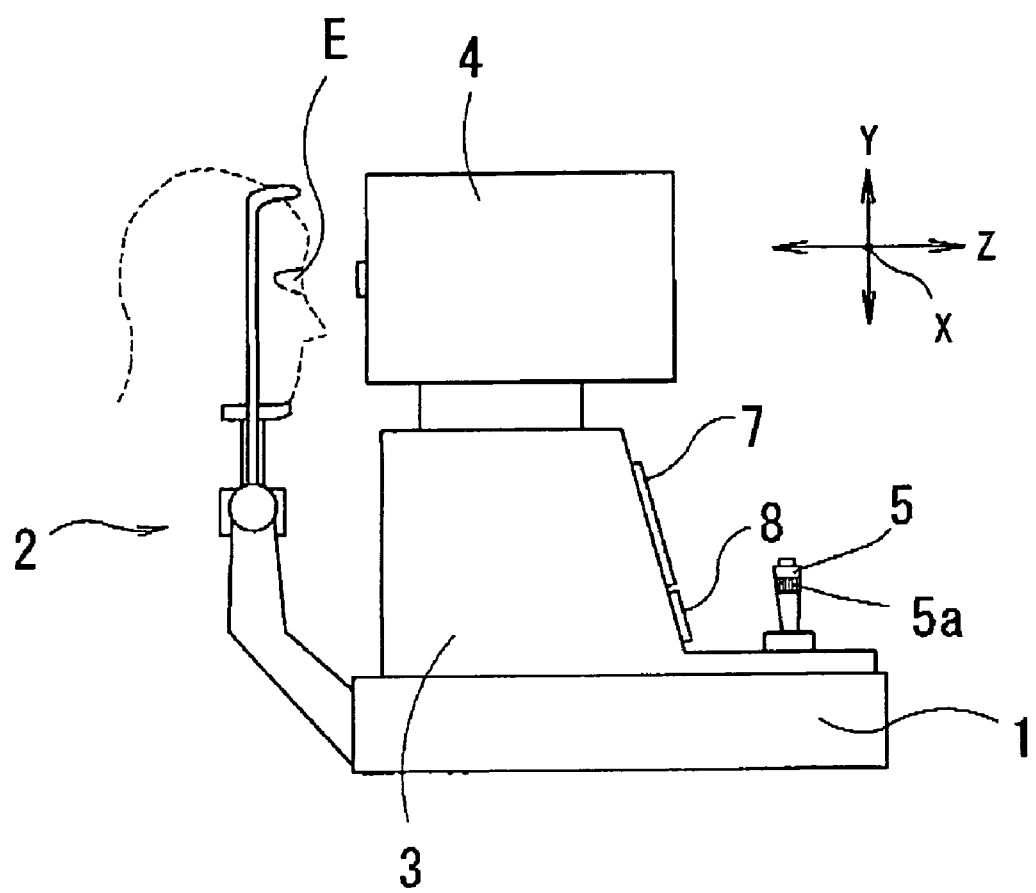
FIG. 1 is a view showing a schematic configuration of an eye refractive power measurement apparatus consistent with one embodiment of the present invention.

A detailed description of one preferred embodiment of an eye refractive power measurement apparatus embodied by the present invention is provided below with reference to the accompanying drawings. FIG. 1 is a view showing a schematic configuration of the eye refractive power measurement apparatus consistent with one embodiment of the present invention. The measurement apparatus is provided with a base 1, a face (head) supporting unit 2 being attached to the base 1, a mobile base 3 being provided movably on the base 1, and a measurement part 4 being provided movably on the mobile base 3 and storing optical systems described later. The mobile base 3 is moved in a right/left direction (an x-direction) and a back/forth direction (a Z-direction) on the base 1 through tilting operation of a joystick 5. In addition, the measurement part 4 is moved in an up/down direction (a Y-direction) on the mobile base 3 through rotating operation of a rotation knob 5a. Arranged on the mobile base 3 are a monitor 7 for displaying various information such as an observation image and a measurement result of an eye E of an examinee, and a switch part 8 provided with switches (keys) for various settings.

Figure 2:
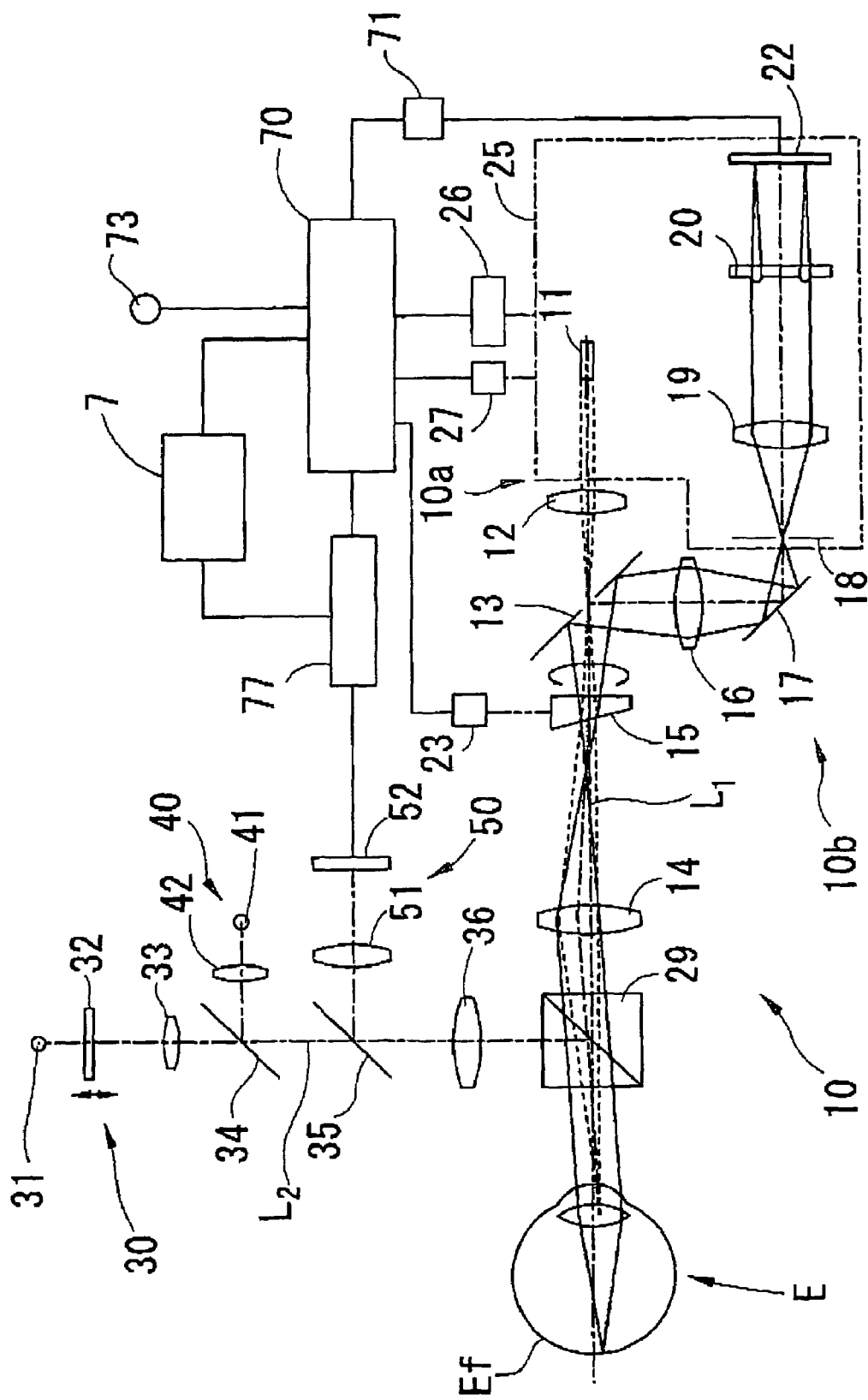
FIG. 2 is a view showing a schematic configuration of optical systems and a control system in the eye refractive power measurement apparatus.

FIG. 2 is a view showing a schematic configuration of optical systems and a control system in the measurement apparatus. A measurement optical system 10 is constituted of a projection optical system 10a for projecting spot-shaped measurement light onto a fundus Ef via a central pupillary portion of the eye E, and a photo-receiving optical system 10b for photo-receiving the measurement light reflected from the fundus Ef via a peripheral pupillary portion of the eye E.

Arranged in the projection optical system 10a on a measurement optical axis L1 are an infrared point light source 11 such as an LED and an SLD, a relay lens 12, a hole mirror 13, a prism 15 which is rotated about the optical axis L1 by a rotation part 23, and an objective lens 14 for measurement. The light source 11 is arranged to have a positional relationship optically approximately conjugate with the fundus Ef, and a hole portion of the mirror 13 is arranged to have a positional relationship optically approximately conjugate with a pupil of the eye E. The prism 15 is prevented from having a positional relationship optically approximately conjugate with the pupil (i.e., arranged at a position aside from an approximately conjugate position), and makes light transmitted therethrough to decenter from the optical axis L1. Incidentally, such constitution may also be employed that a parallel plane plate is inclined to and arranged on the optical axis L1 instead of the prism 15. Disposed between the lens 14 and the eye E is a dichroic mirror (or a half mirror) 29, having a property of reflecting visible light and near infrared light and transmitting infrared light, which reflects near infrared reflection light from an anterior-segment of the eye E toward an observation optical system 50, reflects visible fixation target light from a fixation target presenting optical system 30 (a light source 31) and near infrared alignment target light from an alignment target projection optical system 40 (a light source 41) toward the eye E, and transmits the infrared measurement light from the projection optical system 10a (the light source 11) toward the eye E.

The photo-receiving optical system 10b shares the lens 14, the prism 15, and the mirror 13 in the projection optical system 10a, and includes a relay lens 16 and a reflection mirror 17 which are arranged on the optical axis L1 in a reflecting direction of the mirror 13, and a photo-receiving diaphragm 18, a collimator lens 19, a ring lens 20, and an image-pickup element 22 being a two-dimensional photodetector such as a CCD which are arranged on the optical axis L1 in a reflecting direction of the mirror 17. The diaphragm 18 and the image-pickup element 22 are arranged to have a positional relationship optically approximately conjugate with the fundus Ef. An output of the image-pickup element 22 is inputted to a calculation and control part 70 via an image processing part 71.

Figures 3A, 3B:
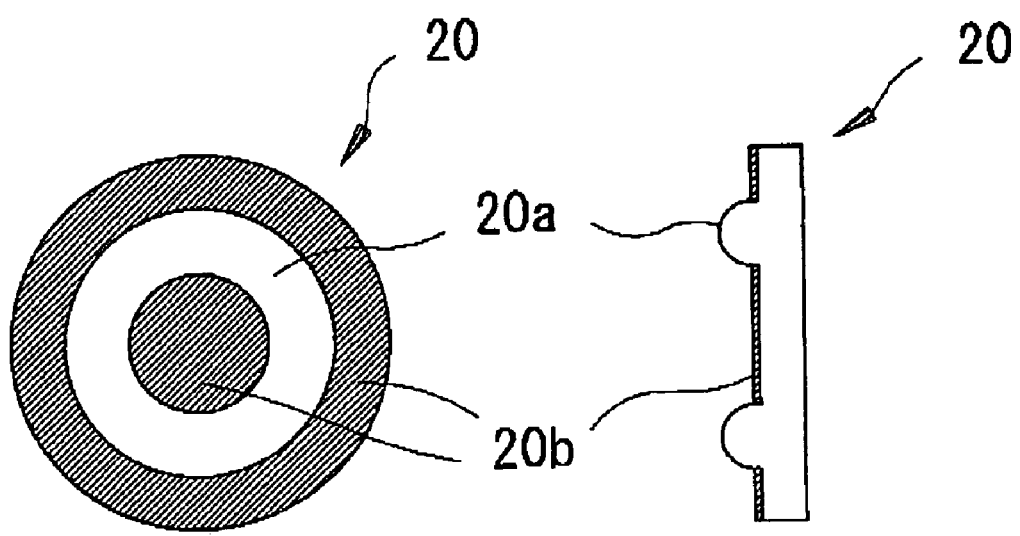
FIGS. 3A and 3B are views showing a schematic configuration of a ring lens.

As shown in FIGS. 3A and 3B, the ring lens 20 is constituted of a lens portion 20a where a cylindrical lens is formed in a ring shape on one side of a transparent plate, and a light shielding portion 20b formed by coating for light shielding which is provided to other portions than the ring-shaped cylindrical lens of the lens portion 20a. Owing to such constitution, a ring-shaped aperture (opening) is formed on the ring lens 20. Incidentally, in the ring lens 20, the ring-shaped aperture (the light shielding portion 20b) is arranged to have a positional relationship optically approximately conjugate with the pupil (which is not necessarily strictly conjugate but may be conjugate with needed accuracy in relation to measurement accuracy). Therefore, the measurement light reflected from the fundus Ef passes through the peripheral pupillary portion and is picked up in a ring shape of a size corresponding to the formed ring-shaped aperture. When parallel light enters the ring lens 20, a ring image of the same size as the ring-shaped aperture is formed on the image-pickup element 22 arranged at a focal point of the ring lens 20. Besides, the ring lens 20 may be constituted of separate members as the ring portion 20a and the light shielding portion 20b. In this ring lens 20, in agreement with an eye with a large pupil diameter (a normal eye), the size of its ring-shaped aperture (referred to simply as a ring size sometimes, hereinafter) is for example 2.0 mm in inside diameter and 2.8 mm in outside diameter on the pupillary surface.

Additionally, the light source 11 in the projection optical system 10a together with the diaphragm 18, the lens 19, the ring lens 20, and the image-pickup element 22 in the photo-receiving optical system 10b are arranged movably in the optical axis L1 direction integrally as a movable unit 25. The movable unit 25 is moved in the optical axis L1 direction by a movement part 26, and is moved in accordance with a spherical refractive error (spherical refractive power) of the eye E, so that the spherical refractive error is corrected and the light source 11, the diaphragm 18, and the image-pickup element 22 are brought to have a positional relationship optically approximately conjugate with the fundus Ef. A travel position (travel amount) of the movable unit 25 is detected by a potentiometer 27. Besides, the mirror 13 and the ring lens 20 are arranged to have a positional relationship optically approximately conjugate with the pupil under a fixed magnification regardless of the travel position (travel amount) of the movable unit 25.

The fixation target presenting optical system 30 includes the visible light source 31, a fixation target plate 32 having a fixation target, a projection lens 33, a dichroic mirror 34 having a property of reflecting near infrared light and transmitting visible light, a half mirror 35, and an objective lens 36 for observation which are arranged on an optical axis L2 being made coaxial with the optical axis L1 by the mirror 29. The light source 31 and the fixation target plate 32 are moved in the optical axis L2 direction to fog the eye E. The fixation target light through illumination of the fixation target by the light source 31 is projected onto the eye E through the lens 33 to the mirror 29. The eye E can thereby perform fixation.

The alignment target projection optical system 40, for projecting an alignment target for detection of an alignment state onto the eye E from the front, shares the mirror 34 to the lens 36 in the fixation target presenting optical system 30 and includes the near infrared point light source 41 such as an LED and an SLD, and a condenser lens 42 which are arranged on the optical axis L2 in a reflecting direction of the mirror 34. The alignment target light from the light source 41 is made approximately parallel light and projected onto the eye E.

The observation optical system 50 shares the lens 36 and the mirror 35, and includes an image-pickup lens 51 and an image-pickup element 52 such as a CCD which are arranged on the optical axis L2 in a reflecting direction of the mirror 35. An output of the image-pickup element 52 is inputted to the monitor 7 and the calculation and control part 70 via an image processing part 77. An image of the anterior-segment of the eye E through an unillustrated near infrared light source for anterior-segment illumination is formed on an image-pickup surface of the image-pickup element 52 through the mirror 29 to the lens 51 to be displayed on the monitor 7 as an observation image. Incidentally, the observation optical system 50 may double as an optical system for detecting an alignment target image formed on a cornea of the eye E and an optical system for detecting the pupil, and in this case, a position of the alignment target image, a position of the pupil and the like are detected by the image processing part 77.

Here will be described operation of the apparatus with the aforementioned constitution. On the occasion of measurement an examiner observes the anterior-segment image and the alignment target image displayed on the monitor 7, and performs alignment of the measurement part 4 with the eye E through operation of the joystick 5 and the rotation knob 5a. Then, when an alignment state of the measurement part 4 with the eye E becomes adequate, a measurement starting switch 73 is depressed to initiate measurement. Besides, the alignment may be automatic alignment where the measurement part 4 is automatically moved based on a detection result on the alignment target image. In this case, a detection system for an alignment state in the Z-direction as well as a mechanism for moving the measurement part 4 in the X-, Y- and Z-directions (a movement part) are provided.

The calculation and control part 70 lights the light source 11 based on an input of a measurement starting signal by the switch 73 and rotates the prism 15 at high speed by the rotation part 23. The measurement light from the light source 11 is projected onto the fundus Ef through the lens 12 to the mirror 29 to form a point-light-source image in a spot shape on the fundus Ef. At this time, a projection image of the hole portion of the mirror 13 on the pupillary surface (projection light on the papillary surface) is decentered and rotated at high speed by the prism 15 which rotates about the optical axis L1.

Light of the point-light-source image formed on the fundus Ef is reflected and scattered to be ejected from the eye E, and is collected by the lens 14 and collected again on an aperture (opening) surface of the diaphragm 18 through the prism 15 which rotates at high speed to the mirror 17. Then, the light is made approximately parallel light by the lens 19 and is made ring-shaped light by the ring lens 20 to be photo-received on the image-pickup element 22. At this time, the measurement light reflected from the fundus Ef is transmitted through the same prism 15 as the time of projection, so that it is conversely scanned in the subsequent optical systems as if there has been no decentering of the projection light and the photo-received light (reflection light) on the pupillary surface.

Figure 4A:
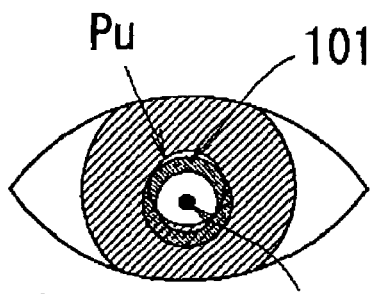
FIGS. 4A to 4I are views showing a relation of projection light and photo-received light on a pupillary surface with photo-received light on an image-pickup element.
Figure 4B:
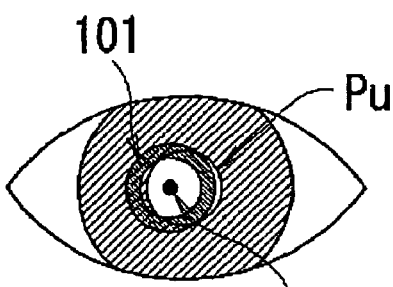
Figure 4C:
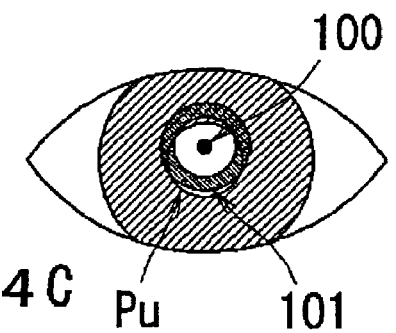
Figure 4D:
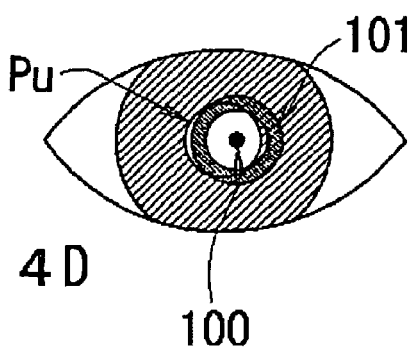
Figure 4E:
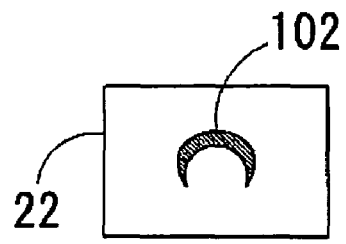
Figure 4F:
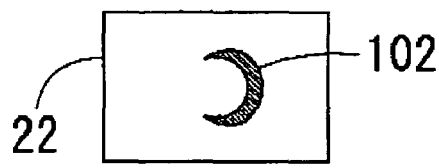
Figure 4G:
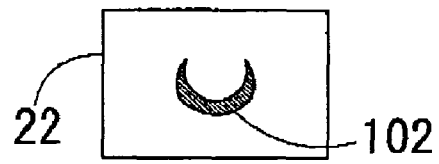
Figure 4H:
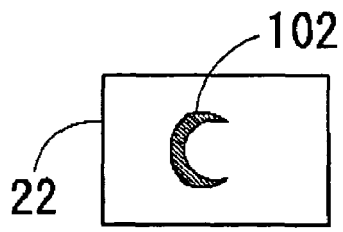
Figure 4I:
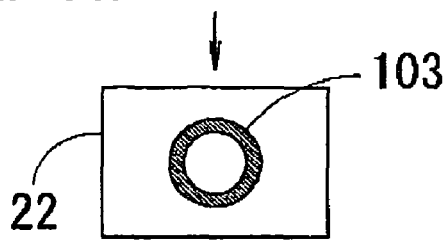

FIGS. 4A to 4I are views illustrating a relation of the projection light and the photo-received light on the pupillary surface with the photo-received light on the image-pickup element 22. As shown in FIGS. 4A to 4D, projection light 100 and photo-received light 101 on the pupillary surface are decentered from and rotated about the center of a pupil Pu at which the optical axis L1 is positioned while maintaining a mutual positional relationship. If capturing the moments, fundus reflection images 102 on the image-pickup element 22 are falcated as shown in FIGS. 4E to 4H; however, by rotating the prism 15 at high speed in a shorter cycle than a storage time of the image-pickup element 22, a ring-shaped image 103 integrating the images can be detected as shown in FIG. 4I. Refractive information can be thereby obtained even if the pupil Pu has a smaller diameter than the photo-received light 101. Further, even in the normal eye, an eye developing a cataract with a non-small pupil and the like, the refractive information can be obtained while maintaining measurement accuracy.

An output signal from the image-pickup element 22 is detected and processed by the image processing part 71 in a case where the eye E is emmetropia, the image-pickup element 22 and the fundus Ef become optically approximately conjugate, and the measurement light reflected from the fundus Ef enters the ring lens 20 as approximately parallel light; therefore, a ring image of the same size and shape as the ring-shaped aperture in the ring lens 20 is formed on the image-pickup element 22. On the other hand, in a case where the eye E has abnormality in a spherical refractive component, a ring image of the size corresponding to an error of the spherical refractive component is formed on the image-pickup element 22. Further, in a case where the eye E has abnormality in an astigmatic refractive component, an oval ring image corresponding to an error of the astigmatic refractive component is formed on the image-pickup element 22. Accordingly, by analyzing the size and shape of the ring image formed on the image-pickup element 22, a refractive error in each meridian direction can be obtained, and by providing predetermined processing thereto, values S (spherical power), C (astigmatic (cylindrical) power) and A (an astigmatic axial angle) can be obtained. Besides, the size and shape of the ring image can be obtained from an edge position of the ring image, the barycenter or a peak position of light intensity level of the ring image, and the like.

Further, the light source 11, the diaphragm 18, the lens 19, the ring lens 20, and the image-pickup element 22 as the movable unit 25 are integrally moved in the optical axis L1 direction to make the ring image on the image-pickup element 22 become thinnest or brightest, or to make an average size of the ring image become the same as the ring size of the ring lens 20, so that the light source 11, the diaphragm 18, and the image-pickup element 22 have a positional relationship optically approximately conjugate with the fundus Ef. Then, the travel position (travel amount) of the movable unit 25 detected by the potentiometer 27 is converted to the error of the spherical refractive component. The refractive error in each meridian direction of the eye E can be obtained as the sum of this error of the spherical refractive component and the refractive error in each meridian direction obtained by the ring image on the image-pick up element 22. With such constitution that the movable unit 25 is moved in the optical axis L1 direction as mentioned above, measurement of a great refractive error can be supported while not scaling down resolution upon ring image analysis and not enlarging the size of a photo-receiving surface of the image-pickup element 22.

Besides, in actual measurement, based on a result of preliminary measurement, the fixation target plate 32 is once brought to have a positional relationship optically approximately conjugate with the fundus Ef, and then moved so as to perform fogging by an adequate amount of diopter, and main measurement is performed in a state where the eye E is fogged. The fixation target light is projected onto the eye E via the mirror 29 arranged on the eye E's side of the prism 15; therefore, the eye E can gaze at the fixation target with stability.

As mentioned above, by rotating the prism 15 prevented from having a positional relationship optically approximately conjugate with the pupil, the projection light and the photo-received light are decentered from and rotated about the pupil center; therefore, measurement can be performed also on the eye with a small pupil diameter. At the same time, influence of noise light due to cataract and the like is reduced to enable accurate measurement. Incidentally, the refractive power is obtained as an average value within the pupil.

In addition, in a constitution without the prism 15 and in a case where a light source with high brightness as well as high coherence such as an SLD is used as a light source for measurement, a speckle noise is caused in the ring image on the image-pickup element 22 by interference of a light source image, and light intensity distribution of the ring image becomes speckled. In this case, it is essential only that the prism 15 is prevented from having a positional relationship optically approximately conjugate with not only the pupil but also the fundus Ef. The spot-shaped measurement light (point-light-source image) projected onto the fundus Ef is thereby decentered and rotated at high speed, so that the speckle noise when using the light source with high coherence (SLD) is neutralized during the storage time of the image-pickup element 22 and the influence thereof can be eliminated. Therefore, by further minimizing the point light source using the light source with high brightness and coherence, a ring width of the ring image can be thinned to enable more precise measurement.

Further, the following advantages are presented by providing the prism 15. When the measurement light from the light source 11 enters the lens 14, it is slightly reflected by a lens surface thereof. In the measurement optical system with the constitution where the measurement light is made to enter the fundus Ef via the central pupillary portion and the measurement light reflected from the fundus Ef is photo-received via the peripheral pupillary portion as mentioned above, when the prism 15 is not arranged, the measurement light from the light source 11 is transmitted through the center of an optical axis of the lens 14; therefore, the reflection light by the lens surface is transmitted through the reflection surface of the mirror 13, the lens 16 and the like, and enters the image-pickup element 22 to be a noise at the time of detecting the fundus reflection image by the image-pickup element 22. By arranging the prism 15 thereto, the measurement light from the light source 11 is decentered by the prism 15 and transmitted through a decentered position on the lens 14 as well. In this case, by designing the lens surface of the lens 14 and the decentered position thereon through which the light is transmitted so that the reflection light from the lens surface of the lens 14 does not enter the mirror surface of the mirror 13 and the subsequent optical systems, the reflection light from the lens surface of the lens 14 is prevented from entering the image-pickup element 22. Besides, the measurement light from the light source 11 is slightly reflected also by the prism 15; therefore, the surface of the prism 15 may be previously inclined to the optical axis L1 so that the reflection light by the prism 15 does not enter the relay lens 16.

Figure 5:
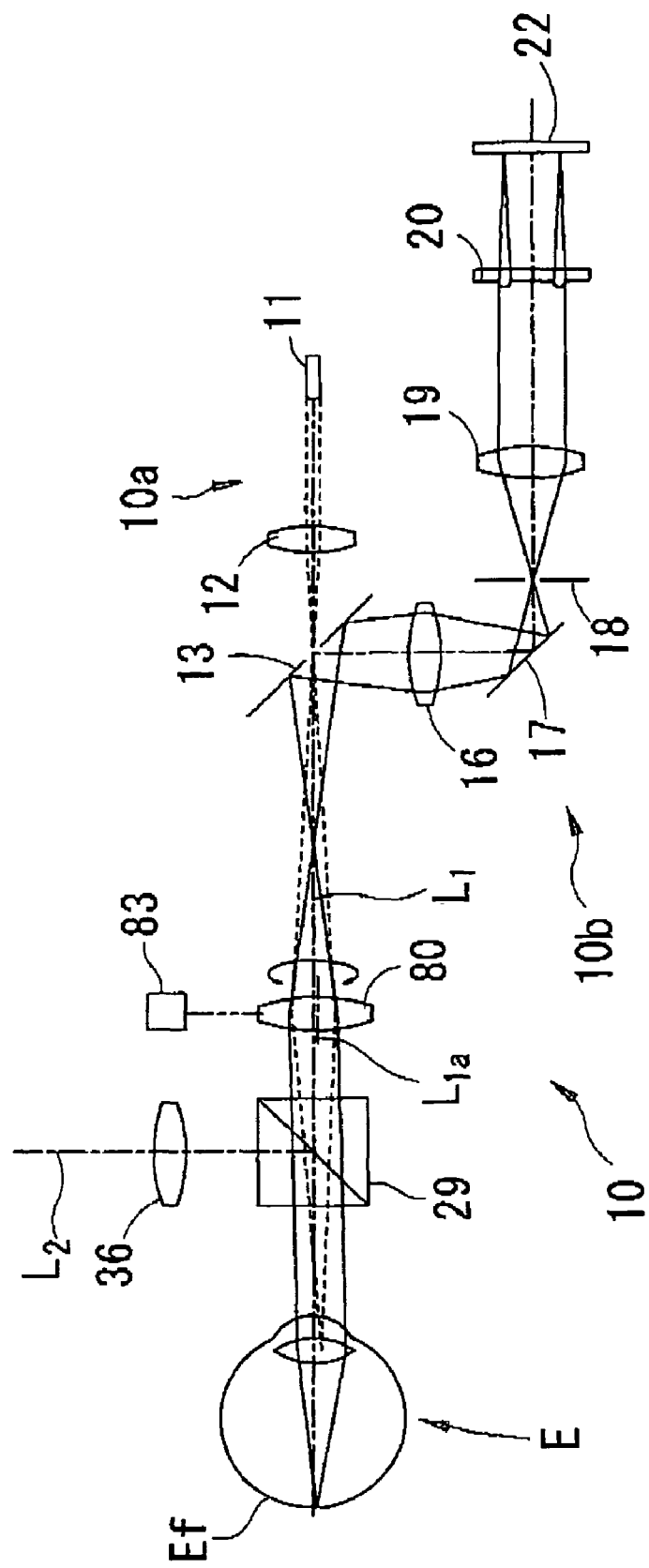
FIG. 5 is a view showing a schematic configuration of a modified embodiment of the measurement optical system in the eye refractive power measurement apparatus.

FIG. 5 is a view showing a schematic configuration of a modified embodiment of the measurement optical system. An optical axis L1a of an objective lens 80 for measurement arranged in a common optical path among the projection optical system 10a and the photo-receiving optical system 10b is made to decenter from the optical axis L1, so that the lens 80 doubles as (substitutes for) the prism 15 as a light deflection member in FIG. 2 in consistent with the previous embodiment. In this case, by rotating the lens 80 at high speed about the optical axis L1 by the rotation part 83, the spot-shaped projection light onto the fundus Ef is decentered from and rotated about the optical axis L1 and the photo-received light is also decentered from and rotated about the optical axis L1 while maintaining the positional relationship with the projection light to enable measurement of the eye with the small pupil diameter. In addition, also by inclining the optical axis L1a of the lens 80 to the optical axis L1, the projection light and the photo-received light can be made to decenter from the optical axis L1 to obtain the same advantages.

Figure 6:
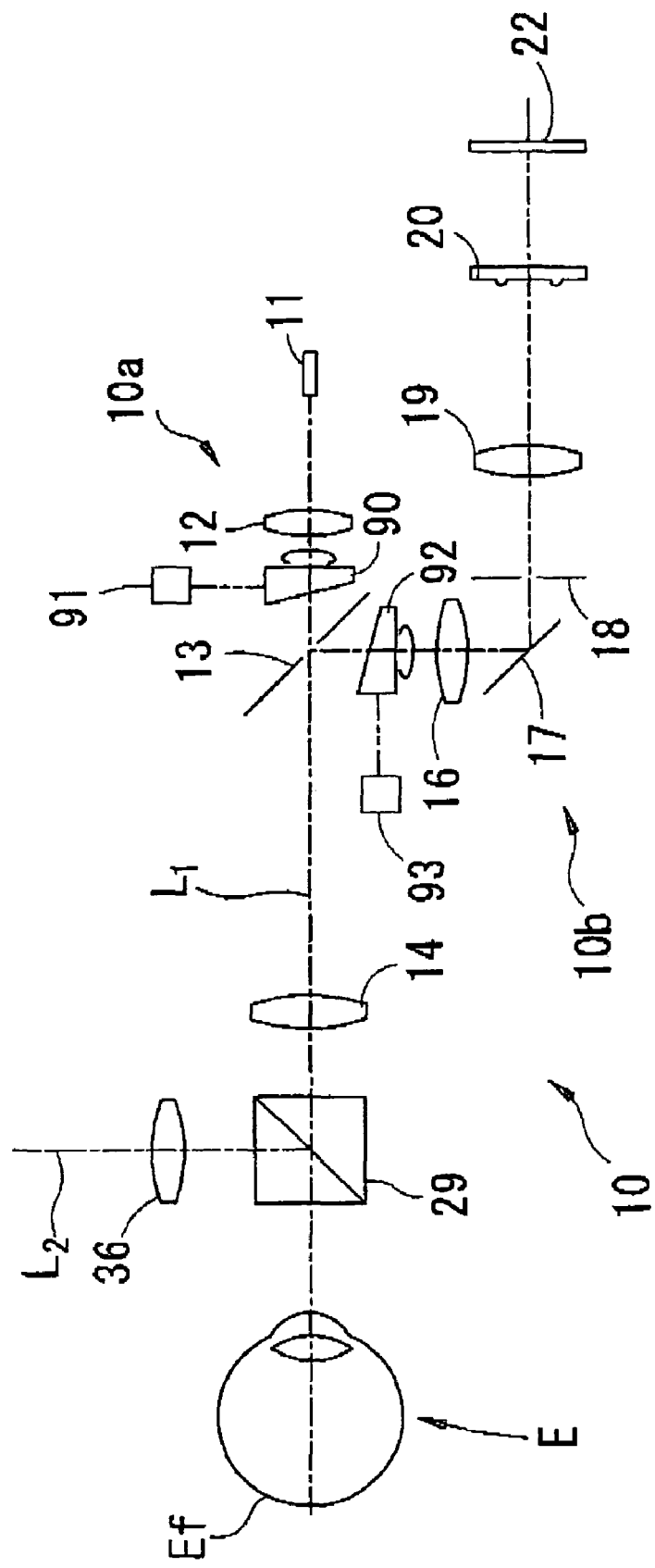
FIG. 6 is a view showing a schematic configuration of another modified embodiment of the measurement optical system in the eye refractive power measurement apparatus.

FIG. 6 is a view showing a schematic configuration of another modified embodiment of the measurement optical system. A first prism 90 as a light deflection member is arranged in an optical path between the lens 12 and the mirror 13 being a dedicated optical path of the projection optical system 10a, and a second prism 92 as a light deflection member is arranged in an optical path between the mirror 13 and the lens 16 being a dedicated optical path of the photo-receiving optical system 10b. Both of the prisms 90 and 92 are prevented from having a positional relationship optically approximately conjugate with the pupil. Then, the prisms 90 and 92 are respectively rotated synchronously about the optical axis L1 by rotation parts 91 and 93 so that their deflection directions are corresponded to each other. Also with such constitution, the same advantages as the previous embodiments can be obtained.

Further, as a modified embodiment of FIGS. 5 and 6, objective lenses are respectively arranged in the projection optical system 10a and the photo-receiving optical system 10b and optical axes of the respective lenses are inclined to or decentered from the optical axis L1 of the respective optical systems. Then, the respective objective lenses are rotated synchronously about the optical axis L1. In this case, the respective objective lenses double as (substitute for) the light deflection members (the first prism and the second prism) in FIG. 6. Also with such constitution, the same advantages as the previous embodiments can be obtained.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus for measuring eye refractive power of an eye of an examinee, the apparatus comprising:
    a measurement optical system including
        a projection optical system including
            a first light deflection member which is placed at a position not conjugate with a pupil of the eye, and is rotated about a measurement optical axis of the measurement optical system at high speed, for projecting measurement light from a measurement light source onto a fundus of the eye through a central pupillary portion of the eye via the first light deflection member and an objective lens, and forming an image in a spot shape on the fundus; and
        a photo-receiving optical system including
            a light shielding member having a ring-shaped aperture, which is placed at a position conjugate with the pupil, and
            a second light deflection member which is placed at a position not conjugate with the pupil, and is rotated about the measurement optical axis at high speed, for forming a ring image on an image-pickup element by the measurement light which is transmitted through the objective lens, the second light deflection member and the ring shaped aperture; and
    a movement unit which corrects a spherical refractive error of the eye to make the measurement light source and the image-pickup element optically conjugate with the fundus,
    wherein the image-pickup element stores the rotating measurement light to obtain the ring image.

2. The eye refractive power measurement apparatus according to claim 1, wherein
    the first and second light deflection members are placed at a positions not conjugate with the fundus, and rotated about the measurement optical axis at high speed.

3. The eye refractive power measurement apparatus according to claim 2, wherein the measurement light source is a light source which has higher brightness and higher coherence than a light emitting diode (LED).

4. The eye refractive power measurement apparatus according to claim 1, further comprising:
    a hole mirror which is placed at a position conjugate with the pupil on an optical path of the projection optical system, wherein the first and second light deflection members are placed on the opposite side of the eye with respect to the hole mirror, the measurement light is projected onto the eye via a hole of the hole mirror, and the measurement light reflected by the hole mirror is guided to the image-pickup element.

5. The eye refractive power measurement apparatus according to claim 1, wherein the first and second light deflection members are any one of a prism, an inclined parallel plane plate, and a lens of which an optical axis is decentered from the measurement optical axis to be placed.

6. An eye refractive power measurement apparatus for measuring eye refractive power of an eye of an examinee, the apparatus comprising:

a measurement optical system including:

a projection optical system for projecting measurement light from a measurement light source onto a fundus of the eye through a central pupillary portion of the eye via the objective lens, and forming an image in a spot shape on the fundus; and a photo-receiving optical system including a light shielding member having a ring-shaped aperture, which is placed at a position conjugate with the pupil, for forming a ring image on an image-pickup element by the measurement light which is transmitted through the objective lens and the ring-shaped aperture;

a light deflection member which is placed at a position not conjugate with the pupil in a common optical path among the projection optical system and the photo-receiving optical system, and is rotated about a measurement optical axis of the measurement optical system at high speed; and a movement unit which corrects a spherical refractive error of the eye to make the measurement light source and the image-pickup element optically conjugate with the fundus, wherein the image-pickup element stores the rotating measurement light to obtain the ring image.

7. The eye refractive power measurement apparatus according to claim 6, wherein the light deflection member is placed at a position not conjugate with the fundus in a common optical path, and rotated about the measurement optical axis at high speed.

8. The eye refractive power measurement apparatus according to claim 7, wherein the measurement light source is a light source which has higher brightness and higher coherence than a light emitting diode (LED).

9. The eye refractive power measurement apparatus according to claim 6, further comprising a hole mirror which is placed at a position conjugate with the pupil on an optical path of the projection optical system, wherein the light deflection member is placed on the eye's side of the hole mirror, the measurement light is projected onto the eye via a hole of the hole mirror, and the measurement light reflected by the hole mirror is guided to the image-pickup element.

10. The eye refractive power measurement apparatus according to claim 1, wherein the light deflection member is any one of a prism, an inclined parallel plane plate, and a lens of which optical axis is decentered from the measurement optical axis to be placed.

* * * * *